US006806464B2

(12) United States Patent
Stowers et al.

(10) Patent No.: US 6,806,464 B2
(45) Date of Patent: Oct. 19, 2004

(54) METHOD AND DEVICE FOR DETECTING AND IDENTIFYING BIO-AEROSOL PARTICLES IN THE AIR

(75) Inventors: Michael Anthony Stowers, Leiden (NL); Arjan Laurens Wuijckhuijse, Zwijndrecht (NL); Johannes Cornelis Maria Marijnissen, Breda (NL); Charles Eliza Kientz, Delft (NL)

(73) Assignee: Technische Universiteit Delft, Delft (NL)

( * ) Notice: Subject to any disclaimer, the term of this patent is extended or adjusted under 35 U.S.C. 154(b) by 0 days.

(21) Appl. No.: 10/450,638

(22) PCT Filed: Dec. 14, 2001

(86) PCT No.: PCT/NL01/00914

§ 371 (c)(1),
(2), (4) Date: Dec. 10, 2003

(87) PCT Pub. No.: WO02/052246

PCT Pub. Date: Jul. 4, 2002

(65) Prior Publication Data

US 2004/0075049 A1 Apr. 22, 2004

(30) Foreign Application Priority Data

Dec. 15, 2000 (NL) .......................................... 1016887

(51) Int. Cl.[7] .......................... B01D 59/44; H01J 49/00

(52) U.S. Cl. ...................... 250/286; 250/287; 250/289; 356/73; 356/72; 356/336

(58) Field of Search ................................ 250/286, 282, 250/287, 289; 356/73

(56) References Cited

U.S. PATENT DOCUMENTS 5,999,250 A * 12/1999 Hairston et al. .............. 356/73
2003/0122070 A1 * 7/2003 Chang et al. ............... 250/292
2004/0024539 A1 * 2/2004 Gard et al. .................... 702/28
2004/0057050 A1 * 3/2004 Beck et al. ................. 356/336

FOREIGN PATENT DOCUMENTS

NL WO 96/31900 * 10/1996

* cited by examiner

*Primary Examiner*—Jack Berman
*Assistant Examiner*—Kalimah Fernandez
(74) *Attorney, Agent, or Firm*—Varnum, Riddering, Schmidt & Howlett LLP

(57) ABSTRACT

In a method for detecting and identifying bioaerosol particles in the air, the bioaerosol particles in a particle stream are selected in an ATOFMS (aerosol time-of-flight mass spectrometer) by means of fluorescence techniques, and only the selected bioaerosol particles are ionized, for instance on the basis of MALDI (matrix-assisted laser desorption/ionization), after which the resulting ions are detected and the bioaerosol particles are identified. The selection of bioaerosol particles takes place by means of laser radiation, generated by a first laser device, of a wavelength which in specific substances in bioaerosol particles effects a fluorescence, after which by means of a fluorescence detector the bioaerosol particles are selected and a second laser device is triggered to emit light of a wavelength which effects the ionization of the bioaerosol particles selected only by the fluorescence detector.

7 Claims, 2 Drawing Sheets

METHOD AND DEVICE FOR DETECTING AND IDENTIFYING BIO-AEROSOL PARTICLES IN THE AIR

Figure 1:
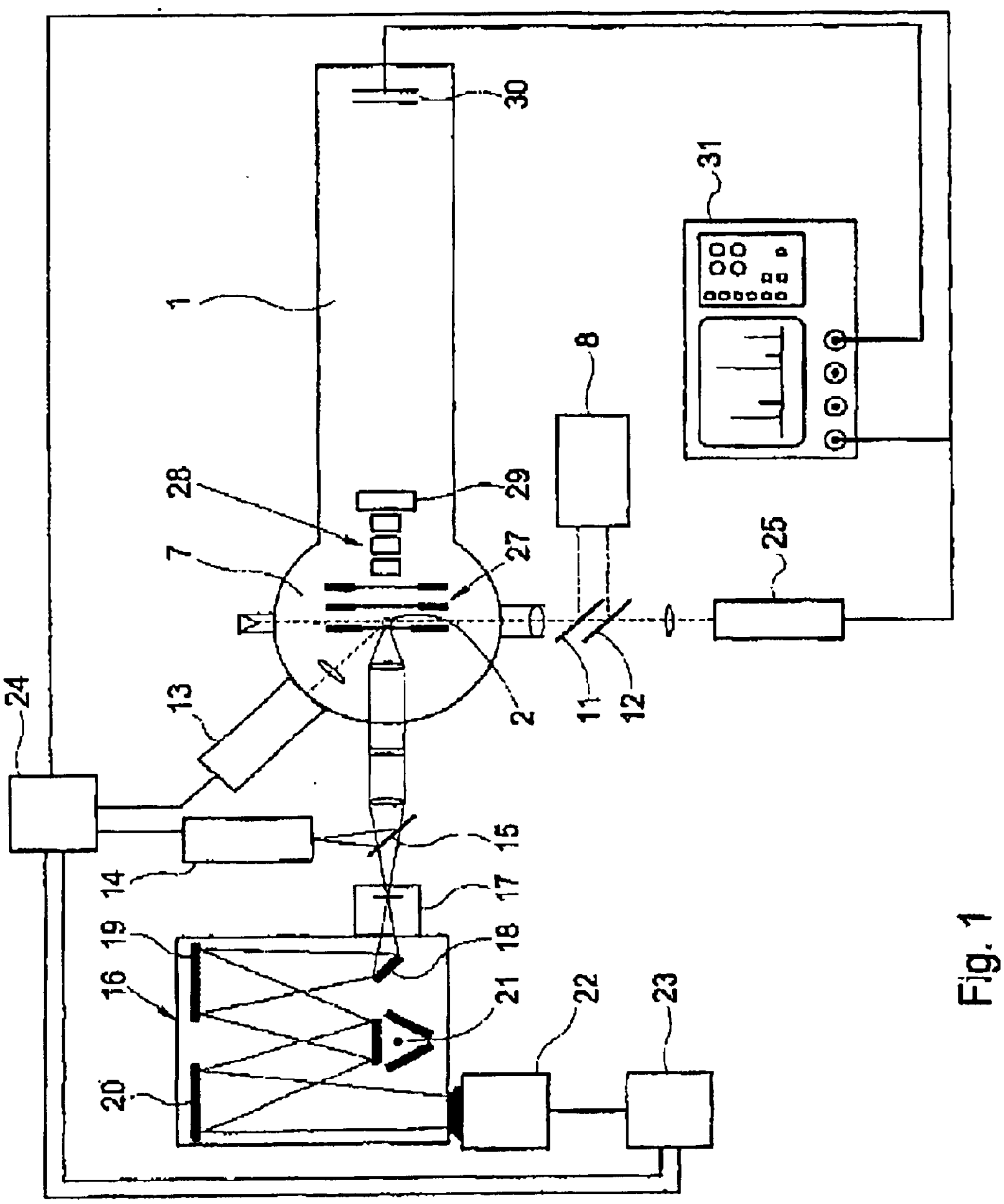

The present invention relates to a method and a device for detecting and identifying bioaerosol particles in the air.

Such a method and a test arrangement used therein are known from an article by M. A. Stowers et al.: Application of matrix-assisted laser desorption/ionization to on-line aerosol time-of-flight mass spectrometry, Rapid Commun. Mass Spectrom. 14, 829–833 (2000). This article indicates that these are two options for "quasi-real-time bioaerosol detection", namely a method in which the intrinsic fluorescence of biomolecules is utilized and methods in which mass spectrometery is applied to ions generated by laser desorption. Because bioaerosol particles form only a small part of the total content of aerosol particles in the air, the known "single particle" fluorescence detectors may be used to indicate whether the aerosol particles are of biological origin or non-biological origin; they are, however, not arranged for identifying bioaerosol particles. The above article therefore describes an identification experiment which starts from bioaerosol particles in a liquid which is nebulized, after which the spray is drawn into an ATOFMS (aerosol time-of-flight mass spectrometer). In this ATOFMS an aerosol particle identification is carried out on the basis of MALDI (matrix-assisted laser desorption/ionization). Even though for this experiment an aerosol has been prepared first, the object of the study indicated in this article is still directed to an identification carried out on real-time basis. In the manner described, however, this cannot be realized in a satisfactory manner, because the air for the greater part contains non-bioaerosol particles. The ATOFMS detection and identification apparatus used is therefore relatively insensitive to bioaerosol particles. In view of the fact that a rapid detection and identification of bioaerosol particles is absolutely necessary under specific conditions, for instance under conditions of biological warfare, the object of the present invention is directed to the aim stated in the above article, namely a rapid on-line bioaerosol particles detection and identification.

A rapid on-line aerosol particle detection and identification, not relating to bioaerosol particle detection and identification, is, for that matter, already known from the international patent application WO96/31900. According to this application an air stream containing particles is passed through an ATOFMS system. A rapid detection and identification of specifically bioaerosol particles is not possible in this manner, because, as mentioned before, there will be relatively few bioaerosol particles in the air, and precisely these particles, as soon as they are spread in the air, must be detected and identified.

In order to solve the above-mentioned problems, in the method according to the invention the bioaerosol particles in a particle stream are selected in an ATOFMS by means of fluorescence techniques, after which successively the selected bioaerosol particles are ionized, the resulting ions are detected and the bioaerosol particles are identified. For the selection of bioaerosol particles the known per se property is utilized that the presence of specific substances, such as, for instance, amino acids, when irradiated with a suitable wavelength, induces a characteristic fluorescence. Thus, the irradiation of tryptophan by UV laser light of 266 nm gives a broad fluorescence in the wavelength range of 300 to 400 nm. Also eligible are the fluorescence spectra of substances, such as tyrosine, NADH or riboflavin (see: Fell et al.; Concentration, size, and excitation power effects and microparticles containing tryptophan and bacteria, SPIE, vol. 3533, pp. 52–62). In general, inorganic and most of the organic substances do not show this characteristic. In order to utilize this property in the method according to the invention, the selection of bioaerosol particles takes place by means of laser radiation, generated by a first laser device, of a wavelength which in specific substances in bioaerosol particles effects a fluorescence, after which by means of a detector for detecting the fluorescence radiation the bioaerosol particles are selected, and a second laser device is triggered to emit light of a wavelength which effects the ionization of the bioaerosol particles selected only by the fluorescence detector. For the first laser device a continuous-wave laser device (cw-laser device) is preferably used, while for the second laser device a pulse laser device is used, the pulses being triggered by the fluorescence detector.

It is efficient in the selection of bioaerosol particles to also utilize the size, that is to say the aerodynamic size, of the aerosol particles. The size of bacteria and viruses is substantially in the range below 20 $\mu$m. Because the aerosol particles enter the central space of the ATOFMS at a given speed, the size of the successive aerosol particles can be determined from the duration of a known distance traversed by an aerosol particle. By directing the laser beam of the first laser device to two successive spots with a known mutual distance, the above duration and hence the size of the aerosol particle can be determined from the light scattered and detected by an aerosol particle. However, the distance between the spots must then be smaller than the mutual distance of the successive particles. For instance, at a distance between the spots of 2.5 mm and a speed of the aerosol particles of approximately 400 m/s the duration between two measurements is approximately 6.25 $\mu$s. To obtain the desired unambiguity between measurements on the above spots, the first laser device is, according to a further aspect of the invention, a two-color continuous-wave laser device, operative at wavelengths of 266 and 532 nm. The wavelength of the light directed to the first spot is 532 nm, and that of the light directed to the second spot is 266. This last wavelength is also such that bioaerosol particles then show fluorescence.

The second laser device is, for instance, an Excimer laser device, operative at a wavelength of 308 nm and, after a proper triggering, ensuring the ionization of only the bioaerosol particles. To this end, the pulses of this laser device, as mentioned before, are triggered by the fluorescence detector. The use of a UV Excimer laser implies that in order to enable the performance of the method described herein on the basis of MALDI, the aerosol particles must be provided with a matrix. According to a further aspect of the invention, the aerosol particles, during or immediately before drawing into the ATOFMS, are therefore provided with such a matrix by evaporation/condensation or sublimitation/condensation. Should an IR (infrared) laser device be used, then this is not necessary.

Figure 2:
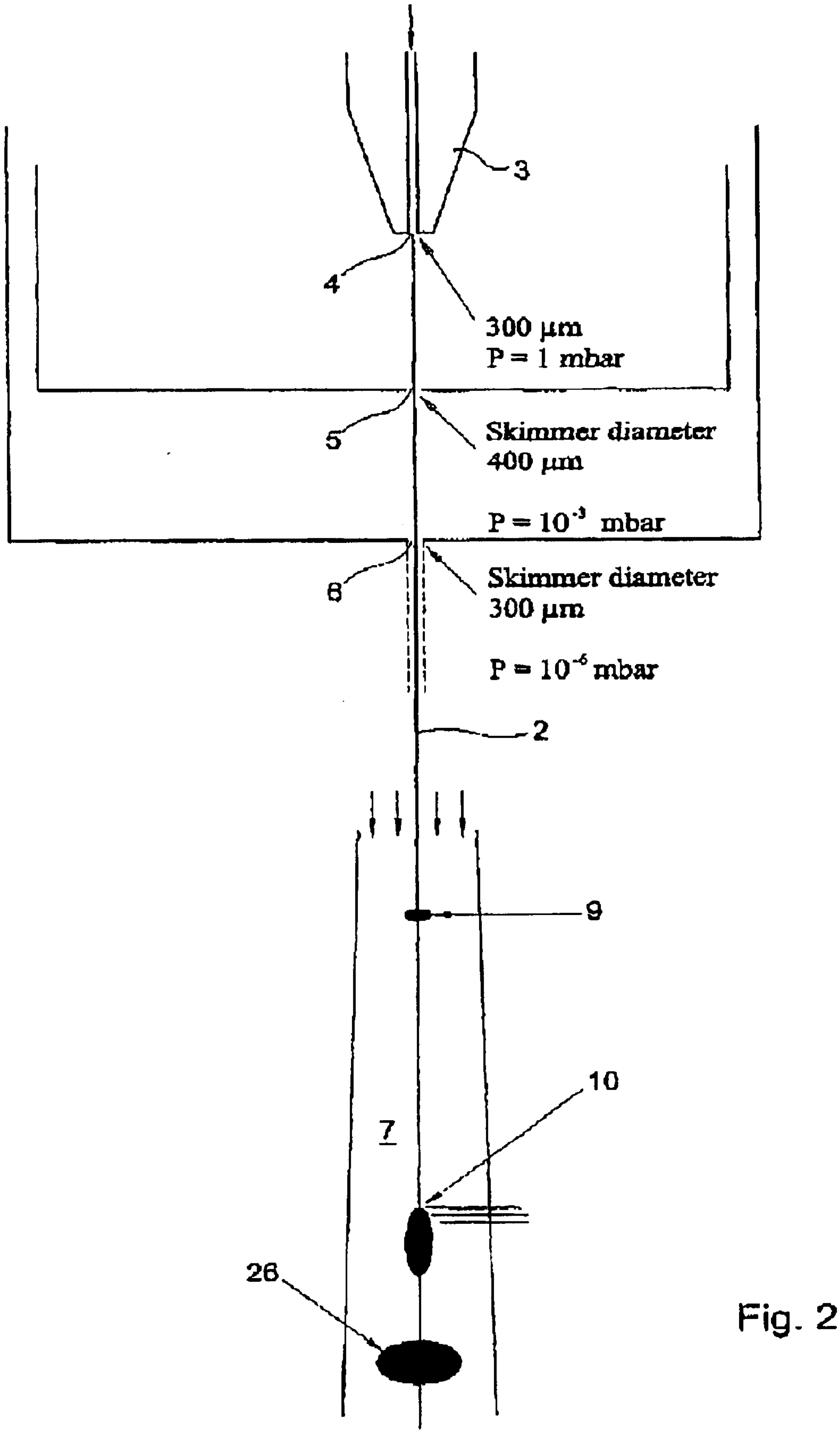

The method and the device according to the invention will now be explained in more detail on the basis of an exemplary embodiment with reference to the accompanying drawing, in which:

FIG. 1 shows a device in which the method for detecting and identifying bioaerosol particles in the air can be used according to the invention; and FIG. 2 diagrammatically shows a part of the distance traversed by a particle stream in the ATOFMS used, in which the locations where particles are subjected to the relevant laser radiation are indicated.

The ATOFMS 1 shown in FIG. 1 is represented in cross-section, that is to say perpendicular to the aerosol particle stream. The aerosol particle stream substantially follows the line 2. Aerosol particles are drawn into the ATOFMS from the air and, in the entrance part of this device, are provided at elevated temperature with a coating, originating from an easily sublimiting substance. It is known to use for this purpose, for instance, picolinic acid or sinapic acid. The aerosol particles are then bundled by means of an aerodynamic lens system, a converging nozzle, and skimmers. FIG. 2 diagrammatically shows how the aerosol particle stream is brought from the nozzle 3 of the above entrance part via an exit opening 4 of 800 $\mu$m and skimmer openings 5 and 6 of respectively 400 and 800 μm into the central space 7 of the ATOFMS. This space is traversed by the aerosol particles one by one, in succession at a specific mutual distance. The speed at which the aerosol particles enter the central space of the ATOFMS is, in the present example, approximately 400 m/s. The pressure in the relevant spaces to be traversed is respectively 1, $10^{-3}$ and $10^{-6}$ mbar. In the central space 7 the aerosol particle stream is first subjected to irradiation by a first laser device 8. In FIG. 1 this is a DPSS (Diode Pumped Solid State) laser, which is a specific type of two-color continuous-wave laser. This laser device 8 sends a light beam of a wavelength of 532 nm to the space 7, that is at the location of the spot 9, as well as light of a wavelength of 266 nm at the location of the spot 10 (see FIG. 2). The light of both wavelengths is deflected by dichroic mirrors 11 and 12. The width of the spot 9 in the direction of the line 2 is approximately 50 μm, the diameter of this spot in the plane perpendicular thereto is approximately 150 μm. The time during which an aerosol particle is exposed is approximately 125 ns. The width of the spot 10 in the direction of the line 2 is approximately 500 μm, the diameter of this spot in a plane perpendicular thereto is again approximately 150 μm. The aerosol particles exposed on the spot 9 scatter the light, while the aerosol particles on the spot 10 both scatter light and emit fluorescence radiation, as far as an aerosol particle is of biological origin. The light scattered by the aerosol particles is detected by the detectors 13 and 14. To this end, these detectors are provided with a photomultiplier tube. The detector 13 directly detects the light scattered from the spot 9. Via a semitransparent mirror 15 the detector 14 detects the light scattered from the spot 10, while the fluorescence radiation is transmitted by this mirror and passed to a fluorescence detector 16. Because the mirror 15 will always transmit a small fraction of the scattered 266 nm radiation, the fluorescence detector 16 comprises at the entrance a band-pass filter 17, which filters this wavelength further away, but transmits the fluorescence radiation located in the range of 300 to 500 nm. The width of the spot 10 in the direction of the line 2 is relatively large. During the first 125 ns, corresponding to the width of the spot 9, the scattered light of an aerosol particle is detected in the detector 14, so that on the basis of the successive observations of the scattered light of the spots 9 and 10 the size of the relevant aerosol particle can be determined. During the following 125 ns the fluorescence detector 16 is released by the detector to examine whether the relevant aerosol particle is actually of biological origin. The remaining time during which the aerosol particle is irradiated on the spot 10 gives the opportunity to increase the reliability of the fluorescence measurement. Besides the various mirrors 18, 19 and 20, the fluorescence detector 16 comprises a diffraction grating 21 and a CCD image recorder 22. When recording the fluorescence radiation, control signals are fed to a trigger circuit 24 by means of a camera control unit 23. Also fed to this trigger circuit 24 are output signals from the two detectors 13 and 14. In the trigger circuit 24 it is determined that an aerosol particle is of biological origin with a specific size, after which a trigger signal is fed to the Excimer laser 25. In other words, as soon as an aerosol particle of a specific size has been recognized as being of biological origin, the Excimer laser device is triggered. That is to say that the Excimer laser device provides a laser pulse, which effects the ionization of the relevant bioaerosol particle on the spot 26. To be sure that the bioaerosol particles are actually ionized, this spot is relatively large: in the direction of the line 2 approximately 300 μm and in the plane perpendicular thereto approximately 500 μm. The distance between the spots 10 and 26 is adjusted to the speed of the aerosol particles and the time required to generate the trigger signal. Via the above dichroic mirrors 11, 12 the Excimer laser pulse is passed to the central space 7 in the ATOFMS. The ionized bioaerosol particles are then accelerated and deflected in the conventional manner by means of electrodes 27 and passed via lenses 28 and a deflection means 29 to the ion detector 30. The result of the mass spectrometry thus performed is shown on a display 31.

The invention is not limited to the exemplary embodiment described herein with reference to the drawing, but comprises all kinds of modifications thereof, of course as far as they fall within the scope of protection of the appended claims. Thus, other types of laser devices may be used, and when the size determination as an additional aid for identifying aerosol particles as being of biological origin is not deemed necessary, it is not necessary to use a two-color laser device. Also, instead of a fluorescence detector 16 with diffraction grating and CCD image recorder, any other known type may be used; diffraction grating and CCD image recorder may be replaced by, for instance, a “gated PMT” with band-pass filters. The spot dimensions are given only by way of example; they may of course be chosen differently, just like the other parameters mentioned in the specification. Because light is scattered, or emitted, by the aerosols to all sides, several detectors may be provided. Strictly speaking, it is not absolutely necessary to use the detectors 13 and 14. Sufficient is the fluorescence detector for recognizing an aerosol particle as being of biological origin and for triggering the Excimer laser. The reliability of such an embodiment, however, will be insufficient in actual practice.

What is claimed is:

1. A method for detecting and identifying bioaerosol particles in the air, in which in an ATOFMS (aerosol time-of-flight mass spectrometer) the bioaerosol particles in a particle stream are selected by means of fluorescence techniques and only the selected bioaerosol particles are ionized, after which successively the resulting ions are detected and the bioaerosol particles are identified.

2. A method according to claim 1, characterized in that the selection of bioaerosol particles takes place by means of laser radiation, generated by a first laser device, of a wavelength which in specific substances in bioaerosol particles effects a fluorescence, after which by means of a fluorescence detector the bioaerosol particles are selected and a second laser device is triggered to emit light of a wavelength which effects the ionization of the bioaerosol particles selected only by the fluorescence detector.

3. A method according to claim 1, characterized in that during or immediately before drawing into the ATOFMS the aerosol particles are provided with a matrix by evaporation/condensation or sublimitation/condensation, after which the selected bioaerosol particles are ionized on the basis of MALDI (matrix-assisted laser desorption/ionization), after which successively the ions are detected and the bioaerosol particles are identified.

4. A device for use of the method according to any claim 1, utilizing an ATOFMS, characterized in that a first laser device is provided for emitting light of a wavelength which in specific substances in bioaerosols effects a fluorescence, and an associated fluorescence detector for detecting the fluorescence radiation, as well as a second laser device, triggered by this detector, for emitting light of a wavelength which effects the ionization of the bioaerosols selected by the fluorescence detector.

5. A device according to claim 4, characterized in that the first laser device is a continuous-wave laser device and the second laser device is a pulse laser device.

6. A device according to claim 4, characterized in that the first laser device is a two-color continuous-wave laser device, operative at wavelengths of 266 and 532 nm.

7. A device according to claim 4, characterized in that the second laser device is an Excimer laser device, operative at a wavelength of 308 nm.

* * * * *